(12) United States Patent
Zinobile (10) Patent No.: US 9,550,714 B2
(45) Date of Patent: Jan. 24, 2017

(54) PUMP AROUND REACTOR FOR PRODUCTION OF ACETIC ACID

(71) Applicant: Celanese International Corporation, Irving, TX (US)

(72) Inventor: Raymond J. Zinobile, Houston, TX (US)

(73) Assignee: CELANESE INTERNATIONAL CORPORATION, Irving, TX (US)

(*) Notice: Subject to any disclaimer, the term of this patent is extended or adjusted under 35 U.S.C. 154(b) by 235 days.

(21) Appl. No.: 13/966,772

(22) Filed: Aug. 14, 2013

(65) Prior Publication Data

US 2014/0012040 A1 Jan. 9, 2014

Related U.S. Application Data

(62) Division of application No. 12/890,383, filed on Sep. 24, 2010, now Pat. No. 8,530,696.

(51) Int. Cl.
*C07C 51/12* (2006.01)

(52) U.S. Cl.
CPC ..................................... *C07C 51/12* (2013.01)

(58) Field of Classification Search
None
See application file for complete search history.

(56) References Cited

U.S. PATENT DOCUMENTS

| | | |
|---|---|---|
| 3,769,329 A | 10/1973 | Knox et al. |
| 4,102,922 A | 7/1978 | Price |
| 4,994,608 A | 2/1991 | Torrence |
| 5,001,259 A | 3/1991 | Smith et al. |
| 5,026,908 A | 6/1991 | Smith et al. |
| 5,144,068 A | 9/1992 | Smith et al. |
| 5,334,755 A | 8/1994 | Yoneda et al. |
| 5,364,963 A | 11/1994 | Minami et al. |
| 5,672,744 A | 9/1997 | Kagotani et al. |
| 5,696,284 A | 12/1997 | Baker et al. |
| 5,731,252 A | 3/1998 | Warner et al. |
| 5,877,347 A | 3/1999 | Ditzel et al. |
| 5,877,348 A | 3/1999 | Ditzel et al. |
| 5,917,089 A | 6/1999 | Howard |
| 5,932,764 A * | 8/1999 | Morris et al. .................. 562/519 |

(Continued)

FOREIGN PATENT DOCUMENTS

| | | |
|---|---|---|
| EP | 0685446 | 12/1995 |
| EP | 0846674 | 6/1998 |

(Continued)

OTHER PUBLICATIONS

International Search Report and Written Opinion for PCT/US2011/051168 mailed Dec. 5, 2011.

(Continued)

*Primary Examiner* — Karl J Puttlitz
(74) *Attorney, Agent, or Firm* — Kilpatrick Townsend & Stockton LLP (57) ABSTRACT

The present invention relates to improved processes for the manufacture of acetic acid. A pump around reactor is used to produce additional heat for the production of steam. The pump around reactor receives a portion of the reaction solution produced by the carbonylation reactor and further reacts that portion with additional carbon monoxide and/or reactants.

13 Claims, 2 Drawing Sheets

(56) References Cited

U.S. PATENT DOCUMENTS

| | | |
|---|---|---|
| 5,942,460 A | 8/1999 | Garland et al. |
| 6,114,576 A | 9/2000 | Leet |
| 6,175,039 B1 | 1/2001 | Voss |
| 6,339,171 B1 | 1/2002 | Singh et al. |
| 6,627,770 B1 | 9/2003 | Cheung et al. |
| 6,657,078 B2 | 12/2003 | Scates et al. |
| 7,005,541 B2 | 2/2006 | Cheung et al. |
| 7,202,382 B2 | 4/2007 | Muskett |
| 7,223,886 B2 | 5/2007 | Scates et al. |
| 7,465,823 B2 | 12/2008 | Bhaskaran et al. |
| 7,576,236 B2 | 8/2009 | Bhaskaran et al. |
| 7,619,113 B2 | 11/2009 | Powell |
| 7,767,848 B2 | 8/2010 | Cawood et al. |
| 2003/0018213 A1 | 1/2003 | Thiebaut |
| 2006/0281944 A1 | 12/2006 | Hosono et al. |
| 2008/0287706 A1 | 11/2008 | Powell |
| 2008/0293966 A1 | 11/2008 | Scates et al. |
| 2009/0107833 A1 | 4/2009 | Warner |
| 2009/0270651 A1 | 10/2009 | Zinobile et al. |
| 2009/0299092 A1 | 12/2009 | Beavis et al. |

FOREIGN PATENT DOCUMENTS

| | | |
|---|---|---|
| JP | 2004-533478 A | 11/2004 |
| WO | WO 2009/103948 | 8/2009 |

OTHER PUBLICATIONS

Written Opinion for PCT/US2011/051168 mailed Aug. 31, 2012.
International Preliminary Report on Patentability mailed Nov. 26, 2012 in corresponding International Application No. PCT/US2011/051168.
J. H. Jones, "The Cativa™ Process for the Manufacture of Acetic Acid," Platinum Metals Review, 44 (3), 2000, pp. 94-105.
Grauβ, et al., "Synthesis of Acetic Acid and Acetic Acid Anhydride from Methanol," Applied Homogeneous Catalysis with Organometallic Compounds, 1996, vol. 1, pp. 104-138 (Editors: Cornelis, B., Herrmann, W., Publisher: VCH, Weinheim, Germany).
Haynes, Anthony, "Catalytic Methanol Carbonylation," Advances in Catalysis, vol. 53, 2010, pp. 1-45.
Office Action for corresponding Chinese Appl. No. 201180054453.7 dated May 5, 2014.
Japanese Notice of Allowance for JP Patent Application No. 2013-530178, dated May 18, 2016.

* cited by examiner

PUMP AROUND REACTOR FOR PRODUCTION OF ACETIC ACID

CROSS REFERENCE TO RELATED APPLICATIONS

This is a divisional of US patent application Ser. No. 12/890,383, filed Sep. 24, 2010, the entirety of which is hereby incorporated by reference.

FIELD OF THE INVENTION

The present invention relates to an improved method for the manufacture of acetic acid and, in particular, to improvements to the acetic acid production system including the addition of a side-stream recovery loop and/or one or more side-stream pump around reactors.

BACKGROUND OF THE INVENTION

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises methyl acetate, water, acetic acid, methyl iodide and the catalyst. Conventional commercial processes for carbonylation of methanol include those described in U.S. Pat. Nos. 3,769,329, 5,001,259, 5,026,908 and 5,144,068, the entire contents and disclosures of which are hereby incorporated by reference. Another conventional methanol carbonylation process includes the Cativa™ process, which is discussed in J. H. Jones, "*The Cativa™ Process for the Manufacture of Acetic Acid*," Platinum Metals Review, 44 (3): 94-105 (2002), the entire contents and disclosure of which is hereby incorporated by reference.

The reaction solution from the carbonylation reactor contains unreacted starting materials as well as components of the reaction medium, including catalyst. U.S. Pat. No. 5,672,744 discloses a process for the preparation of acetic acid, which comprises carbonylating methanol with carbon monoxide in a carbonylation reactor ("first reactor") in the presence of a reaction fluid comprising a rhodium catalyst, methyl iodide, an iodide salt, methyl acetate and water, while continuously withdrawing the reaction fluid from the first reactor and introducing it into a flash zone to separate it into an evaporated part and an unevaporated part, characterized in that a second reactor is provided between the first reactor and the flash zone. Methanol is carbonylated with the carbon monoxide contained in the reaction fluid in a state in which it is dissolved therein in the second reactor with a residence time of 7 to 120 seconds at 150° C. to 250° C., and the carbon monoxide contained in the reaction fluid withdrawn from the first reactor in a state in which it is dissolved therein can be converted into acetic acid in the second reactor through the same carbonylation as that occurring in the first reactor, which enables effective use and high recovery of carbon monoxide.

The carbonylation reaction is exothermic and the heat of the reaction must be regulated to control reaction temperatures. The heat of the reaction typically is transferred to the flasher along with the reaction solution. The flasher operates at a lower pressure than the carbonylation reactor, which results in a temperature decrease of the reaction solution. The heat of the reaction may also be recovered. U.S. Pat. No. 6,175,039 discloses removing the heat of reaction from the highly exothermic process by using a steam boiler heated by the pump-around stream. The heat from the reaction may also be transferred to other systems. U.S. Pat. No. 6,114,576 discloses a process for the production of carboxylic acid in the presence of solid catalyst particles that uses the exothermic heat of reaction with high efficiency in recovering the carboxylic acid product. This process uses indirect heat exchange to transfer the heat of reaction to another stream, without the need for an additional heat transfer fluid such as steam. U.S. Pat. No. 7,465,823 discloses a process and system in which a portion of the heat produced during the production of the acetic acid is transferred to the vinyl acetate production and/or purification process and system to facilitate production and/or purification of the vinyl acetate product.

As will be appreciated by one of skill in the art, there is incentive and a need for improvement to existing processes for the production of acetic acid. The present invention provides some such improvements. The entire contents and disclosure of the references discussed herein are hereby incorporated by reference.

SUMMARY OF THE INVENTION

Embodiments of the present invention are to improved methods for the preparation of acetic acid. In one embodiment of the present invention, a process for producing acetic acid is provided, comprising the steps of: reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a catalyst; introducing at least a portion of the reaction solution to a second reactor to produce a first heat recovery stream; and introducing the first heat recovery stream to the first reactor.

In accordance with another embodiment, the invention is to a process for producing acetic acid comprising the steps of: reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a catalyst; introducing at least a portion of the reaction solution to a second reactor to produce a first heat recovery stream; and passing the first heat recovery stream through a steam generator.

In another embodiment, a process for producing acetic acid is provided, comprising the steps of: reacting carbon monoxide with at least one reactant in a first reactor containing a reaction medium to produce a reaction solution comprising acetic acid, wherein the at least one reactant is selected from the group consisting of methanol, methyl acetate, methyl formate, dimethyl ether and mixtures thereof and wherein the reaction medium comprises water, acetic acid, methyl iodide, and a catalyst; separating at least a portion of the reaction solution to form a first heat recovery stream; separating at least a portion of the first heat recovery stream; and introducing the separated portion of the first heat recovery stream to a second reactor to produce a second heat recovery stream.

Further embodiments of the invention are directed to a system for producing acetic acid, comprising: a first reactor for reacting carbon monoxide, at least one reactant and a reaction medium to produce a first reaction solution comprising acetic acid; a separator for separating the reaction solution into a plurality of derivative heat recovery streams; and a second reactor for reacting carbon monoxide, the at least one reactant and the reaction medium to produce a second reaction solution comprising acetic acid and for recovering steam and/or heat from at least one of the heat recovery streams, wherein the at least one reactant is selected from the group consisting of methanol, methyl acetate, methyl formate, dimethyl ether and mixtures thereof and wherein the reaction medium comprises water, acetic acid, methyl iodide, and a catalyst.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

The present invention relates to improved processes for the manufacture of acetic acid. In particular, the present invention provides for recovering the heat of the reaction in a pump around reactor or extended reactor. The pump around reactor is preferably positioned in a side stream from the carbonylation reactor and a portion of the reaction solution from the carbonylation reactor is fed to the pump around reactor. Carbon monoxide and a reactant selected from the group consisting of methanol, methyl acetate, methyl formate, dimethyl ether and/or mixtures thereof preferably are fed to the pump around reactor. In one embodiment, the pump around reactor contains only the catalyst in the reaction solution, i.e., no additional catalyst is introduced to the pump around reactor. The pump around reactor may extend the carbonylation reaction to produce additional heat of reaction that may be recovered. In one embodiment, the conversion of reactants to acetic acid in the pump around reactor may be lower than the conversion in the methanol carbonylation reactor, e.g., less than 80%, less than 50% or less than 20%.

The product from the pump around reactor preferably passes through a steam generator to produce steam prior to being introduced to the carbonylation reactor. The heat of the reaction in the pump around reactor may be recovered by the steam generator. The product from the pump around reactor may also be cooled through one or more cooling water exchangers, such as, for example, a shell and tube exchanger, prior to being introduced to the carbonylation reactor. The additional cooling water exchangers may also produce steam. In preferred embodiments, the cooling water comprises high grade, captive water that can tolerate, with acceptable degradation, being heated to temperatures of about 150° C. to about 200° C. This superheated captive cooling water could produce steam, in some embodiments, via a steam flash letdown vessel or in other embodiments, by entering another exchanger (e.g., an exchanger where no contact heat exchange steam is generated). In some embodiments, the pump around reactor may generate acetic acid (in addition to the acetic acid formed in the carbonylation reactor). This additional acetic acid may pass through the carbonylation reactor and be recovered.

In addition to recovering the heat of the reaction in the pump around reactor, certain embodiments of the present invention also recover the heat of the reaction from the carbonylation reactor in one or more pump around loops. The pump around loops may comprise one or more heat exchangers. In preferred embodiments of the invention, the pump around loops may be used to regulate the heat of the reaction of the carbonylation process.

In some embodiments, the resulting temperature due to heat of the reaction generated by the pump around reactor may be greater than the temperature due to the heat of reaction from the pump around loops without a pump around reactor. Advantageously, embodiments of the present invention may produce an increase in quantity and quality of steam. Preferably, the steam produced has a pressure, i.e. steam quality, of at least 4 bars, e.g., at least 5 bars, or at least 6 bars.

The present invention may be applied in any methanol carbonylation process. Exemplary carbonylation systems that may be used with embodiments of the present invention include those described in U.S. Pat. Nos. 7,223,886, 7,005,541, 6,657,078, 6,339,171, 5,731,252, 5,144,068, 5,026,908, 5,001,259, 4,994,608 and U.S. Patent Application Pub. Nos. 2008/0287706, 2008/0293966, 2009/0107833, 2009/0270651, the entire contents and disclosures of which are hereby incorporated by reference. A carbonylation system may comprise a carbonylation section and a purification section. Any suitable purification section may be used in combination with any of the embodiments of the present invention. Suitable purification sections are described in the patents referenced above and typically include a light ends column, a drying column, one or more columns for removal of permanganate reducing compounds (PRC's), guard beds, vent scrubbers, and/or heavy ends columns.

Figure 1A:
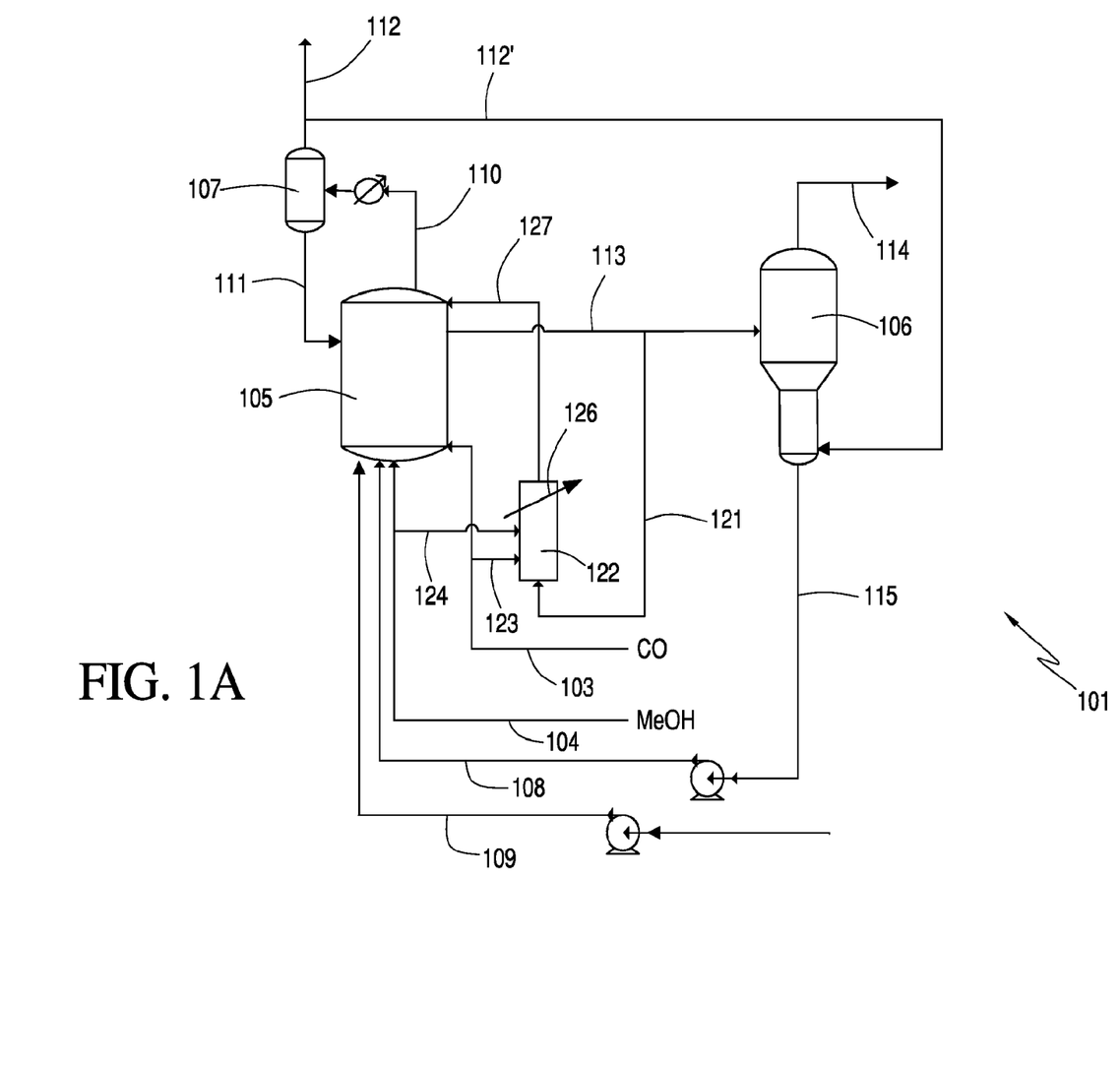
FIG. 1A is a schematic diagram for acetic acid production having a pump around reactor according to one embodiment of the present invention.
Figure 1B:
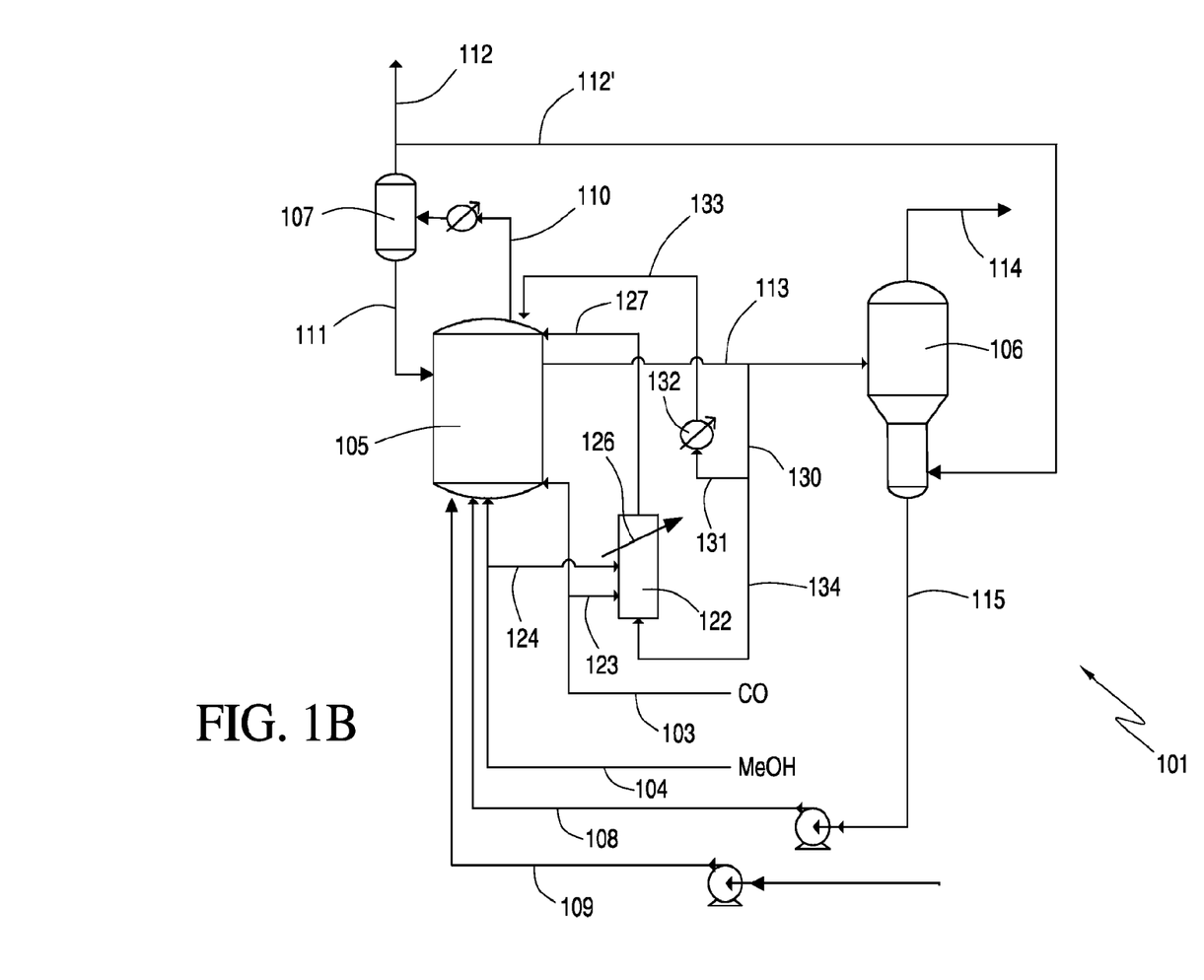
FIG. 1B is a schematic diagram for acetic acid production having a pump around loop from the reaction solution and a pump around reactor according to one embodiment of the present invention.

An exemplary carbonylation section 101 is shown in FIGS. 1A and 1B. The carbonylation section 101 comprises carbon monoxide feed stream 103, reactant feed stream 104, carbonylation reactor 105, which may also be referred to as the "first reactor", flasher 106 and recovery unit 107. Carbon monoxide and at least one reactant are continuously fed by feed streams 103 and 104, respectively, to carbonylation reactor 105. The reactant feed stream 104 may supply at least one reactant selected from the group consisting of methanol, methyl acetate, methyl formate, dimethyl ether and/or mixtures thereof, to the reactor 105. In preferred embodiments, the reactant feed stream 104 may supply methanol and methyl acetate. Optionally, the reactant feed stream 104 may be connected to one or more vessels (not shown) that store fresh reactants for the carbonylation process. In addition, there may be a methyl iodide storage vessel (not shown) and/or catalyst vessel (not shown) connected to the carbonylation reactor 105 for supplying fresh methyl iodide and catalyst as needed to maintain reaction conditions. In other embodiments, the methanol or reactive derivative thereof supplied to carbonylation reactor 105 may be in the form of scrubbed methanol from another location in the system or as a product or by-product of another system.

One or more recycle feed streams from reaction section 101 may be fed to reactor 105 via line 108 and one or more recycle feed streams from a purification section (not shown) may be fed to reactor 105 via line 109. Although two recycle feed streams 108, 109 are shown in FIGS. 1A and 1B, there may be multiple streams that are fed separately to reactor 105. As discussed herein, the recycle feed streams 108 may comprise the components of the reaction medium, as well as residual and/or entrained catalyst and acetic acid.

In some embodiments of the invention, reactant feed stream 104 comprises methanol and/or reactive derivatives thereof. Suitable reactive derivatives of methanol include methyl acetate, dimethyl ether, methyl formate and mixtures thereof. In one embodiment, a mixture of methanol and reactive derivatives of methanol is used as a reactant in the process of the present invention. Preferably, methanol and/or methyl acetate are used as reactants. At least some of the methanol and/or reactive derivatives thereof will be converted to, and hence be present as, methyl acetate in the liquid reaction composition by reaction with acetic acid product or solvent. The concentration of methyl acetate in the liquid reaction composition is preferably in the range of from 0.5 wt. % to 70 wt. %, e.g., from 0.5 wt % to 50 wt. %, or from 1 wt. % to 35 wt. % of the total weight of the liquid reaction composition.

Carbon monoxide feed stream 103 may be essentially pure or may contain small amounts of inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low (e.g., less than 1 bar partial pressure or less than 0.5 bar partial pressure), as its presence may result in the formation of hydrogenation products. The partial pressure of carbon monoxide in the reaction is preferably in the range of from 1 bar to 70 bar, e.g., from 1 bar to 35 bar, or from 1 bar to 15 bar.

In one embodiment, the carbonylation reactor 105 reacts methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]^-$ anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, the entireties of which are hereby incorporated by reference.

When an iridium catalyst is used, the iridium catalyst may comprise any iridium-containing compound that is soluble in the liquid reaction composition. The iridium catalyst may be added to the liquid reaction composition for the carbonylation reaction in any suitable form that dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)^-_2Br_2]^-H+$, $[Ir(CO)_2I_4]^-H^+$, $[Ir(CH_3)I_3(CO)_2]^-H^+$, $Ir_4(CO)_{12}$, $IrCl_3 \cdot 3H_2O$, $IrBr_3 \cdot 3H_2O$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid ($H_2IrCl_6$). Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

A halogen co-catalyst/promoter is generally used in combination with the Group VIII metal catalyst component. Methyl iodide is a preferred as the halogen promoter. Preferably, the concentration of halogen promoter in the liquid reaction composition is in the range 1 wt. % to 50 wt. %, preferably 2 wt. % to 30 wt. %.

The alkyl halide promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

Water may be formed in situ in the liquid reaction composition, for example, by the esterification reaction between methanol reactant and acetic acid product. In some embodiments, water is introduced to the carbonylation reactor 105 together with or separately from other components of the liquid reaction composition. Water may be separated from other components of the reaction composition withdrawn from the reactor and may be recycled in controlled amounts to maintain the required concentration of water in the liquid reaction composition. Preferably, the concentration of water maintained in the liquid reaction composition is in the range of from 0.1 wt. % to 16 wt. %, e.g., from 1 wt. % to 14 wt. %, or from 1 wt. % to 10 wt. % of the total weight of the reaction composition.

In accordance with a preferred carbonylation process of the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

As shown in FIGS. 1A and 1B, carbonylation reactor 105 is preferably a stirred vessel, (e.g., continuous stirred-tank reactor (CSTR), or bubble-column type vessel, with or without an agitator (agitator not shown)), within which the reaction medium is maintained, preferably automatically, at a predetermined level. This predetermined level may remain substantially constant during normal operation. Into carbonylation reactor 105, methanol, carbon monoxide, and sufficient water may be continuously introduced as needed to maintain at least a finite concentration of water in the reaction medium. In one embodiment, carbon monoxide (e.g., in the gaseous state) is continuously introduced into carbonylation reactor 105. Carbon monoxide feed 103 is introduced at a rate sufficient to maintain the desired total reactor pressure. The temperature of carbonylation reactor 105 may be controlled using a pump around reactor and/or pump around loops, as illustrated in the embodiments shown in FIGS. 1A and 1B.

Acetic acid is typically manufactured in a liquid phase reaction at a temperature of from about 160° C. to about 220° C. and a total pressure of from about 20 bar to about 50 bar. In some embodiments of the invention, the carbonylation reactor 105 is operated at a temperature from about 150° C. to about 250° C., e.g., from 155° C. to 235° C., or from 160° C. to 220° C. Certain embodiments of the present invention are directed to methods for the synthesis of acetic acid where the carbonylation reaction temperature is performed at temperatures elevated to above about 190° C. Exemplary reaction temperatures for carbonylation are about 190° C. to about 225° C., including about 200° C. to about 220° C. The elevated reaction temperature may facilitate lowering of the reactor catalyst concentration and increase production rates. The pressure of the carbonylation reaction is preferably from 10 to 200 bar, more preferably 10 to 100 bar, and most preferably 15 to 50 bar.

In a typical carbonylation process, carbon monoxide is continuously introduced into the carbonylation reactor, preferably via a distributor, and desirably below the agitator, which may be used to stir the contents of the reactor. The gaseous feed preferably is thoroughly dispersed through the reacting liquid by this stirring means. In preferred embodiments of the invention, a gaseous/vapor purge stream 110 is vented from the carbonylation reactor 105 to at least prevent buildup of gaseous by-products, inerts and maintain a set carbon monoxide partial pressure at a given total reactor pressure. The temperature of carbonylation reactor 105 may be controlled and the carbon monoxide feed is introduced at a rate sufficient to maintain the desired total reactor pressure. Gaseous purge stream 110 may be scrubbed with acetic acid and/or methanol in recovery unit 107 to recover low boiling components. In some embodiments, the gaseous purge stream 110 may be condensed and fed to a recovery unit 107, which may return low boiling components 111 to the top of reactor 105. The low boiling components 111 may comprise methyl acetate and/or methyl iodide. Carbon monoxide in the gaseous purge stream 110 may be purged in line 112 or fed via line 112' to the base of flasher 106 to enhance rhodium stability.

Carbonylation product is drawn off the carbonylation reactor 105 at a rate sufficient to maintain a constant level therein and is transported to flasher 106 via reaction solution 113. Reaction solution 113 is preferably a liquid stream. In general, as reaction solution 113 is withdrawn from carbonylation reactor 105, the temperature of reaction solution 113 may be from about 150° C. to about 250° C. In flasher 106, the carbonylation product is separated in a flash separation step to obtain a crude product stream 114 comprising acetic acid, and a catalyst recycle stream 115, comprising a catalyst-containing solution, which preferably is recycled to the carbonylation reactor 105 via stream 108. The catalyst-containing solution predominantly contains acetic acid, the rhodium catalyst and the iodide salt, along with lesser quantities of methyl acetate, methyl iodide and water, as discussed above. In certain embodiments, crude product stream 114 is transferred to the purification section (not shown) for recovering acetic acid. One or more recycle streams from the purification section may be returned to the carbonylation reactor 105 via line 109.

In FIGS. 1A and 1B, a portion of the reaction solution 113 is withdrawn via line 121 and directed to a pump around reactor 122, also referred to as the "second reactor." The flow rate of the reaction solution 113 that is withdrawn, or "withdraw rate", is a function of production rate and may vary. In certain embodiments, the withdraw rate is controlled based on reactor level. In some embodiments, the amount of withdrawn reaction solution 113 introduced to the pump around reactor 122 via line 121 may be from 20% to 100%. During start up of carbonylation reactor 105, it is preferred that about 100% of the reaction solution 113 be directed to pump around reactor 122 and returned to reactor 105. Pump around reactor 122 is used (via heat exchanger) to heat (using steam) the reaction solution. In some start up embodiments, a small quantity of carbon monoxide (CO) is injected via the pump around reactor 122 (e.g., a portion of stream 123 that is CO). However, during start up, pump around reactor 122 does not actively inject methanol or methyl acetate. Under design rate, steady state conditions, it is preferred that less than 50% of reaction solution 113 be directed to pump around reactor 122 (i.e., one pump around reactor loop system). In certain embodiments, less than 25%, e.g., less than 20%, of reaction solution 113 may be introduced to pump around reactor 122. However, introducing lesser amounts may reduce the quantity of steam that may be generated. In other embodiments, the acetic acid production system design can include two or more pump-around reactor loop systems. In some such embodiments having two pump-around reactor loop systems where the total of pump around loops was likewise the same two systems, under design rate, steady state conditions, about 70% of reaction solution 113 can be directed to the combination of both pump-around reactor loop systems.

The pump around reactor 122 may be a pipe reactor, tubular reactor, fluidized bed, or CSTR. In a preferred embodiment, the pump around reactor 122 is a tubular reactor of constant diameter. The shell of the reactor can be comprised of any suitable material known in the art, for example a nickel-molybdenum alloy such as HASTELLOY™ B-3™ alloy (Haynes International) or a zirconium alloy such as Zirc™ 702 alloy (United Titanium Inc.). In accordance with various embodiments of the invention, the pump around reactor 122 may contain mixing enhancers such as, for example, baffles, packing, distributors, venturi(s), and multiple passes.

The portion of reaction solution 113 in line 121 may be an aliquot portion and may comprise one or more of catalyst, dissolved carbon monoxide, one or more reactants, water, and halogen promoters. The residual catalyst from carbonylation reactor 105 preferably catalyzes the reaction in pump around reactor 122. In addition to the portion of the reaction solution in line 121, a portion of carbon monoxide feed stream 103 may be fed to pump around reactor 122 via line 123. In some embodiments, carbon monoxide in line 123 may be fed to pump around reactor 122 in a controlled manner in an amount that is about 0.1% to about 10%, based on the total carbon monoxide fed to the carbonylation reactor 105, and more preferably about 0.5% to 5%.

A portion of the reactant feed stream 104 may also be fed to pump around reactor 122 via line 124. In certain embodiments of the present invention, the percentage of methanol in portion 121 fed to pump around reactor 122 varies depending on the conversion of methanol to acetic acid. In one embodiment, the percentage of reactants in the feed via line 124 to pump around reactor 122 is from 0.1% to 10%, based on the entire amount of reactants fed to the system, e.g., from 0.2% to 5% or from 0.25% to 2.5%. In preferred embodiments, additional reactants may be fed via line 124 to pump around reactor 122. In one embodiment, methanol is fed to pump around reactor 122 as the reactant. Reactants in line 124 may be fed to the pump around reactor 122 in a controlled manner in an amount that is about 0.1% to 10%, based on the total reactants fed to the carbonylation reactor 105, and more preferably about 0.5% to 5%. The reactants in line 124 may be preheated before being fed to pump around reactor 122.

In one embodiment, the reactants fed to pump around reactor 122 may be provided from one or more vent scrubbers. Vent scrubbers may use methanol to remove low boiling point components from vents, such as methyl iodide. Without being bound by theory the additional methyl iodide may be useful in promoting the reaction in the pump around reactor 122.

The feed materials, which includes lines 121, 123, and 124, in the pump around reaction have a residence time of from about 0.2 seconds to 120 seconds, e.g., 1 second to 90 seconds, or seconds to 60 seconds. As used herein, "residence time" for the pump around reaction refers to the time the feed materials are injected into the pump around reactor 122 through passage from the steam generator 126. It should be understood that the reaction from the pump around reactor may continue as the product is introduced into carbonylation reactor 105.

In preferred embodiments, pump around reactor 122 is operated at a temperature higher than carbonylation reactor 105. In one embodiment, pump around reactor 122 is operated a temperature that is at least 5° C. higher than carbonylation reactor 105, and more preferably at least 10° C. higher. In certain embodiments, pump around reactor 122 is operated at a temperature from about 150° C. to about 250° C., e.g., from 155° C. to 235° C., or from 160° C. to 225° C. In further embodiments of the invention, the pump around reactor 122 is operated at an absolute pressure from about 15 atmospheres to about 50 atmospheres.

The reaction in the pump around reactor 122 is exothermic. The exothermic heat of the reaction in pump around reactor 122, as computed from standard heats of formation of gaseous carbon monoxide, liquid methanol and liquid acetic acid depends on the amount of acetic acid produced and design rates. The temperature resulting from the heat of reaction produced in pump around reactor 122 may be reduced and heat, therefore, may be recovered by steam generator 126. Steam generator 126 may be directly coupled or closely coupled with pump around reactor 122 so that the heat of the reaction may be efficiently recovered. In some embodiments, pump around reactor 122 may comprise a reactor section and a steam generator section. Steam generator 126 produces steam that may be used to drive other systems in the carbonylation process or other chemical units, such as, for example, anhydride production units and/or ester units. Heat recovery stream 127 exits steam generator 126 at a lowered temperature, but at a temperature not below the carbonylation reaction temperature (e.g., from 160° C. to 190° C.). In some embodiments, the reaction in the pump around reactor may continue past steam generator 126. In preferred embodiments, quantity of steam may range from 3 to 30 tns/hr and quality of steam may range from 4 to 13 barg. The quantity of steam produced by steam generator 126 may vary based on the flow from pump around reactor 122 and the net change in temperature from the exothermic reaction in the pump around reactor 122 through steam generator 126, and the pressure quality of steam being generated. The heat recovery stream 127 may be introduced to the upper section of carbonylation reactor 105, and preferably is introduced above the point at which reaction solution 113 is withdrawn. The heat recovery stream 127 may comprise one or more of acetic acid, methyl iodide, methyl acetate, unreacted methanol, water, carbon monoxide and residual catalyst. In one embodiment, the heat recovery stream 127 may contain a greater concentration of acetic acid than portion 121 fed to pump around reactor 122.

Although not shown, heat recovery stream 127 may pass through one or more heat exchangers, such as, for example, cooling water exchangers. Preferably, these heat exchangers may control the heat of the reaction of reactor 105. In some embodiments, these additional heat exchangers generate an amount of steam.

FIG. 1B is a schematic diagram of another embodiment of the present invention. As shown in FIG. 1B, a portion of reaction solution 113 is withdrawn in line 130. As described above with regard to FIG. 1A, the amount of reaction solution 113 that is withdrawn may vary. A subportion in line 131 may be taken from line 130 and may be pumped around in a loop through a heat exchanger 132 and returned to carbonylation reactor 105 via heat recovery stream 133. Although one loop is shown in FIG. 1B, there may be multiple loops each having one or more heat exchangers. In one embodiment, subportion 131 enters heat exchanger 132 at a temperature of from about 160° C. to about 250° C. (e.g., from 160° C. to 235° C., or from 160° C. to 220° C.) and exits heat exchanger 132 as heat recovery stream 133 at a temperature below the carbonylation reaction temperature (e.g., below about 155° C., or 30° C. to 150° C.).

Heat exchanger 132 preferably controls the heat of reaction in the carbonylation reactor 105. Preferably heat exchanger 132 is a cooling water exchanger that provides trim cooling to remove heat of the reaction from the carbonylation reactor 105. In addition, heat exchanger 132 may also produce steam. In other embodiments, heat exchanger 132 may be used to provide heat to the carbonylation reactor 105 during start up. The heat recovery stream 133 may be introduced to the top of carbonylation reactor 105 and is preferably introduced above the point at which the reaction solution 113 is withdrawn. Although it is shown in FIG. 1B that one portion of the reaction solution is taken (i.e., subportion 131), multiple portions may be taken and separately provided to pump around reactor 122 and heat exchanger 132.

Another subportion in line 134 may be fed to pump around reactor 122, as described above and illustrated in FIG. 1B. The flow ratio between subportion 131 and subportion 134 is preferably from 10:1 to 1:10, e.g., from 5:1 to 1:5 or from 2:1 to 1:2. This ratio may vary depending on the need to control the heat of the reaction of the carbonylation reactor 105 versus the need to produce additional steam through steam generator 126. Although not shown in FIG. 1B, in some embodiments of the invention, one or more valves, regulators or pumps may be used to control the flow of the liquid in line 130 between subportion 131 and subportion 134. This may allow greater flow to pass though to pump around reactor 122 in order to shift additional heat recovery, as necessary, to the loop. Although not shown in FIG. 1A or 1B, in some embodiments of the invention, a combination of manual and automatic isolation valves in the pump around loops allow for independent isolation of one loop (e.g., for maintenance), while the other loop(s) and carbonylation reactor 105 remain operational. In addition, in various embodiments of the invention, one or more additional heat exchangers or coolers may be present in locations throughout the system (e.g., one or more additional coolers can be positioned in recycle feed stream 108).

The relative amount of acetic acid in heat recovery stream 127 from the pump around reactor 122 is a function of residence time. In one embodiment of the present invention, the relative amount of acetic acid in heat recovery stream 127 from the pump around reactor 122 may be at least 0.5% greater than the acetic acid in heat recovery stream 133, and more preferably at least 2.5% or greater. In terms of ranges, the relative amount of acetic acid in heat recovery stream 127 is from 1% to 10% more than in the heat recovery stream 133.

Parameters such as the residence time in the pump around loop and measured temperatures, flow(s) and/or measured pressures with controlled raw material flow rate additions may be optimized to a desired configuration. In some embodiments of the present invention, the second reactor is positioned upstream of heat recovery steam generation (heat exchanger). This configuration will generate a split higher grade (pressure) of steam and/or a greater quantity of steam via stage heat recovery from one or more heat exchangers (steam generators) in the pump around loop than that which can be recovered from bulk average reactor temperature.

In the interest of clarity, not all features of an actual implementation for the processes used to carbonylate methanol to acetic acid are described in this specification. It will be appreciated by those of skill in the art that in the development of any such actual embodiment, numerous implementation-specific decisions must be made to achieve the specific goals, such as compliance with system-related and business-related constraints, which will vary from one implementation to another. Moreover, it will be appreciated that such a development effort may be complex and time-consuming, but would nevertheless be a routine undertaking for those of ordinary skill in the art having the benefit of this disclosure.

In order that the invention disclosed herein may be more efficiently understood, non-limiting examples are provided below. The following examples describe various embodiments of the inventive methods.

EXAMPLE 1

Using a simulated model, the exothermic heat of the reaction in the pump around reactor was determined based on the amount of methanol in the flow to the pump around reactor. Table 1 illustrates that as the wt. % of methanol increases in the flow to the pump around reactor (from of the portion of the reaction solution from the carbonylation reactor), the temperature of the pump around reactor effluent increases, as does the overall change in temperature ($\Delta T$). This increase would be initiated at the injection point(s) of the methanol to the pump around solution. As used in Examples 1 and 2, the phrase "change in temperature" is not limited to a variation in temperature, but rather is an expression of equivalent energy as the sensible heat added to the pump around stream.

TABLE 1

| PUMP AROUND REACTOR $\Delta T$ (° C.) POTENTIAL INCREASE | | |
| --- | --- | --- |
| Run | wt. % of Methanol Added | $\Delta T$ (° C.) Equivalent by Reaction |
| 1 | 0.25 | 3.9 |
| 2 | 0.33 | 5.2 |
| 3 | 0.5 | 7.8 |
| 4 | 0.67 | 10.4 |
| 5 | 1.0 | 15.6 |
| 6 | 1.3 | 20.8 |
| 7 | 2.0 | 31.3 |

As shown in Table 1 above, when 0.33% of the total flow to the pump around reactor is methanol, the change in temperature, as sensible heat energy equivalent added, is about 5° C.

EXAMPLE 2

Using a simulated model, the exothermic reaction in the pump around reactor was shown to achieve a net increase of steam, based on a 7.5 kg/cm² g steam quality standard. As the change in temperature increased and the reactor effluent passing through the heat exchanger increased, the amount of steam produced also increased. Different runs were simulated at a total flow through the pump around reactor of 800 tons per hour (TPH), 600 TPH and 400 TPH.

TABLE 2

| NET INCREASE OF 7.5 kg/cm²g STEAM (in Tons/hr) | | | |
| --- | --- | --- | --- |
| $\Delta T$ (° C.) (Sensible Heat Equivalent Added) | 800 TPH | 600 TPH | 400 TPH |
| 5 | 2.8 | 2.3 | 1.7 |
| 10 | 5.5 | 4.6 | 3.3 |
| 15 | 8.3 | 6.9 | 5.0 |
| 20 | 11.1 | 9.2 | 6.7 |
| 25 | 13.8 | 11.5 | 8.4 |
| 30 | 16.6 | 13.8 | 10.0 |

As shown in Table 2, the total flow (e.g., 800 TPH, 600 TPH, or 400 TPH), determines the net increase in steam production, with a basis of the same heat exchanger area. As the change in temperature continues to increase, there will be a continued increase in the net production of steam. This is a function of reaction residence time as well as the physical size (area) of steam generator 126 versus heat exchanger 132.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. Furthermore, those of ordinary skill in the art will appreciate that the foregoing description is by way of example only, and is not intended to limit the invention.

The invention claimed is:

1. A process for producing acetic acid, comprising the steps of:
    reacting carbon monoxide with at least one reactant in a first reactor containing a reaction medium to produce a reaction solution comprising acetic acid,
    wherein the at least one reactant is selected from the group consisting of methanol, methyl acetate, methyl formate, dimethyl ether and mixtures thereof and
    wherein the reaction medium comprises water, acetic acid, methyl iodide, and a catalyst;
    separating at least a portion of the reaction solution to form a first heat recovery stream;
    separating at least a portion of the first heat recovery stream;
    introducing the separated portion of the first heat recovery stream to a second reactor and recovering the heat from the second reactor to produce a second heat recovery stream; and
    introducing the second heat recovery stream directly to the first reactor.

2. The process of claim 1, further comprising the step of: introducing the first heat recovery stream to the first reactor.

3. The process of claim 1, wherein the relative amount of acetic acid in the second heat recovery stream is at least 0.5% greater than in the first heat recovery stream.

4. The process of claim 1, wherein the second reactor is a pipe reactor.

5. The process of claim 1, wherein the second reactor is a tubular reactor.

6. The process of claim 1, wherein the second reactor is a fluidized bed.

7. The process of claim 1, wherein the second reactor is a continuous stirred-tank reactor.

8. The process of claim 1, wherein the second reactor is operated at a temperature higher than the first reactor.

9. The process of claim 1, wherein the second reactor is operated at a temperature from 150° C. to 250° C.

10. The process of claim 1, wherein the second reactor is operated at a pressure of from 15 atmospheres to 50 atmospheres.

11. The process of claim 1, wherein the separated portion of the first heat recovery stream has a residence time in the second reactor of from 0.2 seconds to 120 seconds.

12. The process of claim 1, further comprising the step of:
    feeding carbon monoxide to the second reactor in an amount of from 0.1% to 10% of the carbon monoxide fed to the first reactor.

13. The process of claim 1, wherein the residual catalyst from the first reactor catalyzes the reaction in the second reactor.

* * * * *